United States Patent
Kubota et al.

(10) Patent No.: US 7,662,098 B2
(45) Date of Patent: Feb. 16, 2010

(54) ULTRASONIC PROBE AND ULTRASONIC DEVICE

(75) Inventors: Jun Kubota, Nagareyama (JP); Akira Sasaki, Ichikawa (JP); Hiroshi Furuhata, Kasukabe (JP); Kazunari Ishida, Kasiwa (JP); Shinichiro Umemura, Kokubunji (JP); Takashi Azuma, Kokubunji (JP); Katsunori Asafusa, Matsudo (JP)

(73) Assignees: Hitachi Medical Corporation, Tokyo (JP); Jikei University, Tokyo (JP)

( * ) Notice: Subject to any disclaimer, the term of this patent is extended or adjusted under 35 U.S.C. 154(b) by 164 days.

(21) Appl. No.: 10/543,916

(22) PCT Filed: Jan. 29, 2004

(86) PCT No.: PCT/JP2004/000812

§ 371 (c)(1),
(2), (4) Date: Jul. 29, 2005

(87) PCT Pub. No.: WO2004/066856

PCT Pub. Date: Aug. 12, 2004

(65) Prior Publication Data

US 2006/0173321 A1 Aug. 3, 2006

(30) Foreign Application Priority Data

Jan. 31, 2003 (JP) ............................. 2003-024252
Oct. 10, 2003 (JP) ............................. 2003-352464

(51) Int. Cl.
*A61B 8/00* (2006.01)
*A61H 1/00* (2006.01)

(52) U.S. Cl. ............................. 600/439; 600/459; 601/2
(58) Field of Classification Search ................. 600/439, 600/459, 437, 407; 367/153, 155; 601/2
See application file for complete search history.

(56) References Cited

U.S. PATENT DOCUMENTS

| 5,307,816 | A | | 5/1994 | Hashimoto et al. | |
| 5,558,092 | A | * | 9/1996 | Unger et al. ................ | 600/439 |
| 5,560,362 | A | * | 10/1996 | Sliwa et al. ................. | 600/439 |
| 5,694,936 | A | * | 12/1997 | Fujimoto et al. ........... | 600/439 |
| 5,823,962 | A | * | 10/1998 | Schaetzle et al. ........... | 600/439 |
| 6,425,867 | B1 | * | 7/2002 | Vaezy et al. ................ | 600/439 |
| 6,454,713 | B1 | * | 9/2002 | Ishibashi et al. ........... | 600/439 |

(Continued)

FOREIGN PATENT DOCUMENTS

EP 0 701 840 3/1996

(Continued)

OTHER PUBLICATIONS

Japanese Office Action (and English translation) issued in corresponding Japanese Patent Application No. 2005-504740.

*Primary Examiner*—Eric F Winakur
*Assistant Examiner*—Katherine L Fernandez
(74) *Attorney, Agent, or Firm*—Antonelli, Terry, Stout & Kraus, LLP.

(57) ABSTRACT

An ultrasound probe comprises therapeutic transducers which include a plurality of arrayed first transducer elements and emit therapeutic ultrasounds to a subject, and diagnostic transducers which include a plurality of arrayed second transducer elements and emit diagnostic ultrasounds to the subject and receive the diagnostic ultrasounds, wherein the therapeutic transducers are stacked over the diagnostic transducers.

16 Claims, 12 Drawing Sheets

U.S. PATENT DOCUMENTS 6,635,017 B1 * 10/2003 Moehring et al. .......... 600/439

FOREIGN PATENT DOCUMENTS

| | | |
|---|---|---|
| EP | 0 701 840 A1 | 3/1996 |
| JP | 03-151952 | 6/1991 |
| JP | 5-220152 | 8/1993 |
| JP | 8-131454 | 5/1996 |

* cited by examiner

Two-frequency ultrasound outputs from composite probe

Therapeutic ultrasound/diagnostic ultrasound switching system

ULTRASONIC PROBE AND ULTRASONIC DEVICE

TECHNICAL FIELD

The present invention relates to an ultrasound probe and an ultrasound apparatus for use in ultrasound therapy.

BACKGROUND ART

In an ultrasound apparatus, therapeutic ultrasounds are emitted via a diagnostic probe kept in contact with the body surface of a subject, and ultrasound images (e.g. tomograms and M-mode images) are reconstructed on the basis of reflected echo signals generated from the subject. Also, a target region is uninvasively treated by emitting therapeutic ultrasounds onto the subject via a therapeutic probe.

In performing an ultrasound therapy, a diagnostic probe and a therapeutic probe are usually arranged alongside each other on the body surface of the subject in order to emit therapeutic ultrasounds while checking the target region by its ultrasound images (see, e.g., Japanese Patent Application Laid-Open No. 5-220152).

However, arranging a diagnostic probe and a therapeutic probe alongside each other on the body surface as in the conventional practice results in a difference in scanning coordinates between the diagnostic ultrasounds and the therapeutic ultrasounds according to the difference between the contact positions of the two probes. Moreover, since the contact positions of the two probes are determined by the operator as desired, the difference in scanning coordinates is not constant. Therefore, while finding out the difference in scanning coordinates between the two probes on every occasion of therapeutic action, the coordinate position of the target region is determined on the basis of ultrasound images acquired with the diagnostic probe, the coordinate position is converted into the coordinate system of the therapeutic probe, and therapeutic ultrasounds are emitted onto the target region accordingly. As a result, particular care should be taken in manipulating the therapeutic probe and the diagnostic probe, inviting inconvenience in the use of probes.

DISCLOSURE OF THE INVENTION

An object of the present invention is to realize an ultrasound probe and an ultrasound apparatus suitable for use in ultrasound therapy.

In order to solve the problem noted above, an ultrasound probe pertaining to the invention comprises therapeutic transducers, including a plurality of arrayed first transducer elements, for emitting therapeutic ultrasounds to a subject; and diagnostic transducers, including a plurality of arrayed second transducer elements, for emitting diagnostic ultrasounds to the subject and receiving the diagnostic ultrasounds reflected by the subject, wherein the therapeutic transducers and the diagnostic transducers are stacked.

According to the invention, since it is possible to so position the scanning coordinates of therapeutic ultrasounds from the therapeutic transducers and those of diagnostic ultrasounds from the diagnostic transducers as to coincide with each other, the control accuracy of the position of irradiation with the therapeutic ultrasounds can be enhanced. Also, e.g., the center of the aperture of the therapeutic transducers can be so positioned as to coincide with that of the aperture of the diagnostic transducers.

Further, an ultrasound apparatus pertaining to the invention comprises the aforementioned ultrasound probe; a therapeutic transmitting device for generating driving signals for the therapeutic transducers; a diagnostic transmitting device for generating driving signals for the diagnostic transducers; an image constructing device for reconstructing ultrasound images on the basis of reflected echo signals received by the diagnostic transducers; and a detecting means for detecting the state of the therapy of the subject with the therapeutic ultrasounds, wherein the therapeutic transmitting device has a warning function to output warning information on the basis of the state of the therapy detected by the detecting means.

According to the invention, since it is possible to detect the progress of therapy with therapeutic ultrasounds, the operator is enabled to stop the ultrasound therapy by an alarm sounded or a warning message displayed, resulting in increased operating ease of the ultrasound apparatus. Also, the target region can be prevented from being excessively irradiated with therapeutic ultrasounds.

BEST MODES FOR CARRYING OUT THE INVENTION

A first embodiment to which an ultrasound probe and ultrasound apparatus according to the present invention are applied will be described. This embodiment is one example of an ultrasound probe in which a plurality of diagnostic transducers are stacked over the ultrasound emitting faces of therapeutic transducers.

Figure 1:
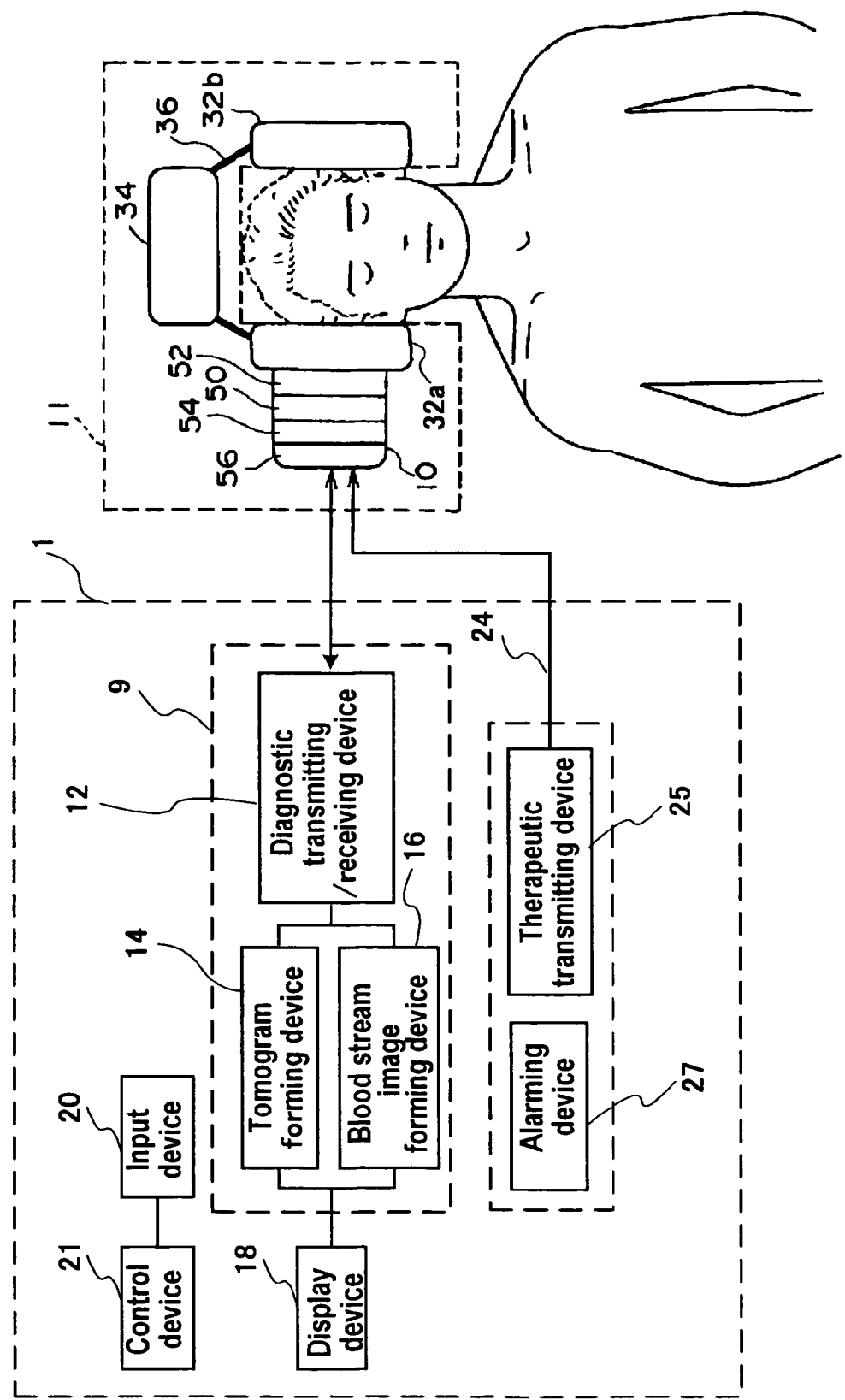
FIG. 1 is a configurative diagram of an ultrasound apparatus of a first embodiment according to the present invention.

As shown in FIG. 1, an ultrasound apparatus 1 is configured of a diagnostic ultrasound unit 9, a therapeutic ultrasound transmitting unit 24, a display device 18, an input device 20, a control device 21 and so forth. The diagnostic ultrasound unit 9 is provided with a diagnostic transmitting/receiving device 12 having a diagnostic transmitting device, an image composing device including a tomogram forming device 14 and a blood stream image forming device 16, and so forth. The therapeutic ultrasound transmitting unit 24 is provided with a therapeutic transmitting device 25, an alarming device 27 and so forth. And the diagnostic transmitting/receiving device 12 and the therapeutic transmitting device 25 are connected to an ultrasound probe 10.

The diagnostic transmitting/receiving device 12 generates driving signals for transmitting diagnostic ultrasounds to the ultrasound probe 10, and receives reflected echo signals outputted from the ultrasound probe 10. The tomogram forming device 14 reconstructs tomograms on the basis of the reflected echo signals. The blood stream image forming device 16 figures out the blood stream velocity from the Doppler shift of reflected echo signals and reconstructs blood stream images on that basis.

The therapeutic transmitting device 25 generates driving signals for emitting therapeutic ultrasounds to the ultrasound probe 10. The alarming device 27 has a warning function of sounding a buzz or displaying a warning message at an input instruction. The display device 18 displays tomograms and blood stream images on the display screen of a monitor. The input device 20 is formed to have a keyboard and a pointing device, such as a mouse.

The ultrasound probe 10 emits ultrasounds for diagnostic and therapeutic purposes, and is contained in a headset 11. The headset 11 comprises the ultrasound probe 10 and a probe cooling device including water bags 32a and 32b, a circulation path 36 and a radiator device 34. The water bags 32a and 32b are formed in a bag shape, holding a coolant (e.g. water) within. Incidentally, the water bags 32a and 32b need not be bag-shaped. The circulation path 36 guides water in the water bags 32a and 32b to the radiator device 34. The radiator device 34 radiates the heat of the guided water into the external atmosphere.

Detailed configuration of the ultrasound apparatus 1 composed in this way will be described together with its operations. First, the headset 11 is put on the head of the subject. This causes the water bags 32a and 32b of the headset 11 to be fixed in a state of being in contact with the outer skin (e.g. near the temples) of the subject's head. And the ultrasound probe 10 is brought into contact with the rear face of the water bag 32a.

Then, driving signals are supplied to the ultrasound probe 10 from the diagnostic transmitting/receiving device 12. The supplied driving signals cause diagnostic ultrasounds to be emitted towards the subject from the ultrasound probe 10. The emitted diagnostic ultrasounds are reflected or scattered by living tissues or the blood stream within the head. Those diagnostic ultrasounds are received by the ultrasound probe 10 as reflected echo signals. The received reflected echo signals are reconstructed into tomograms by the tomogram forming device 14. The reconstructed tomograms are displayed on the monitor of the display device 18. By observing the displayed tomograms, the position of the target region (e.g. cerebral thrombosis) can be accurately identified.

And the input of the position of the target region (e.g. cerebral thrombosis) in the tomograms is set from the input device 20. On the basis of the positional coordinates of the cerebral thrombosis so set, driving signals are generated by the therapeutic transmitting device 25. The generated driving signals are supplied to the therapeutic transmitting device 25 of the ultrasound probe 10. This enables the cerebral thrombosis to be irradiated with therapeutic ultrasounds from the ultrasound probe 10 to dissolve the cerebral thrombosis uninvasively.

When the cerebral thrombosis is dissolved, the blood vessel is reopened to let the blood flow. The blood which has begun to flow causes diagnostic ultrasounds to be reflected or scattered as reflected echo signals. The Doppler shift of those reflected echo signals is figured out by the blood stream image forming device. On the basis of the Doppler shift so figured out, blood stream images (e.g. two-dimensional Doppler blood stream images or pulse Doppler FFT measured images) are reconstructed and displayed.

In such an ultrasound apparatus, if the diagnostic probe and the therapeutic probe were separate, the two probes would have to be arranged alongside each other and brought into contact with the water bag 32a. In this case, as differences in scanning coordinates would occur between diagnostic ultrasounds and therapeutic ultrasounds according to the difference between the two probes in contact position, care should be taken of the manipulation of the therapeutic probe and the diagnostic probe in performing ultrasound therapy. Unlike that, in the present embodiment, the target region can be precisely irradiated with therapeutic ultrasounds by using an ultrasound probe integrally formed by stacking diagnostic transducers and therapeutic transducers.

Figure 2:
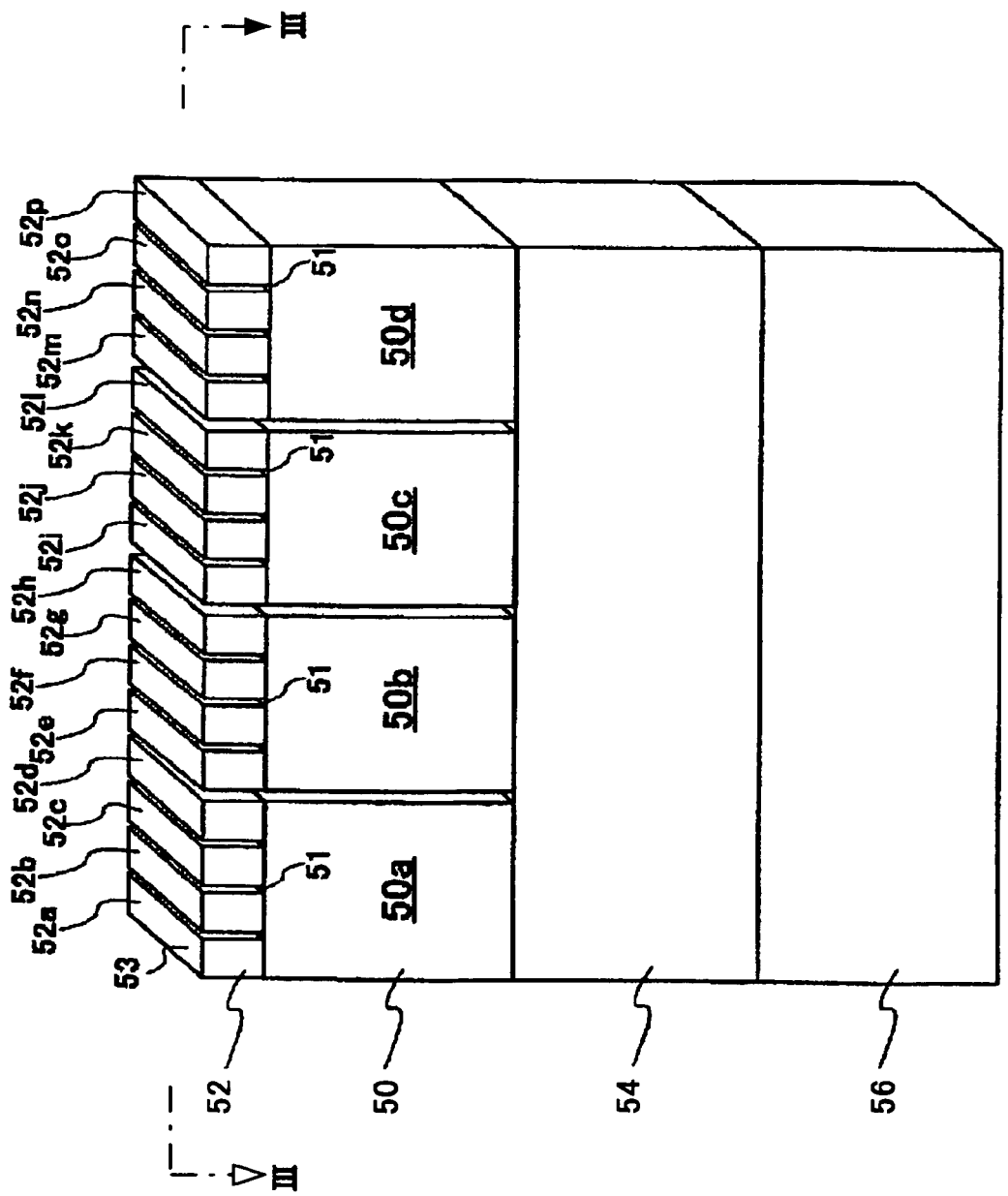
FIG. 2 is a perspective view schematically showing the ultrasound probe of the first embodiment according to the invention.

Next, the ultrasound probe 10 will be described in detail. As shown in FIG. 2, the ultrasound probe 10 is composed by stacking diagnostic transducers 52, therapeutic transducers 50, a backing material 54 and a cooling device 56 in this order from the subject side. The therapeutic transducers 50 generate ultrasounds of a relatively low frequency (e.g. about 500 kHz) while the diagnostic transducers 52 generate ultrasounds of a relatively high frequency (e.g. about 2 MHz). Therefore, as the ultrasounds generated by the diagnostic transducers 52 are more difficult to be transmitted by an obstacle than the ultrasounds generated by the therapeutic transducers 50 are, the diagnostic transducers 52 are stacked over the therapeutic transducers 50 so that the former can be closer to the subject.

The therapeutic transducers 50 are formed by arraying a plurality of transducer elements 50a through 50d. The therapeutic transducer elements 50a through 50d, each formed of a piezoelectric ceramic cuboid, are arrayed at equal intervals with the longitudinal directions of ultrasound emitting faces 51 being parallel to one another. The arrayed therapeutic transducer elements 50a through 50d convert the driving signals from the therapeutic ultrasound transmitting unit 24 into mechanical transducers, and deflect them to emit therapeutic ultrasounds to the target region (e.g. cerebral thrombosis).

The diagnostic transducers 52 are formed by arraying a plurality of transducer elements 52a through 52p. The diagnostic transducer elements 52a through 52p, each formed of a piezoelectric ceramic cuboid, are made smaller than the transducer elements 50a through 50d of the therapeutic transducers 50 in order to enhance the resolution of the tomograms to be reconstructed. And more than one of diagnostic transducer elements 52a through 52p are distributed over the ultrasound emitting faces 51. For example, as shown in FIG. 2, the diagnostic transducer elements 52a through 52d are distributed over the ultrasound emitting face 51 of the therapeutic transducer element 50a. Thus, the reverse faces of the diagnostic transducer elements 52a through 52d to an ultrasound emitting face 53 are joined to the ultrasound emitting faces 51 of the therapeutic transducer element 50a. And the diagnostic transducer elements 52a through 52d are arranged at equal intervals in the shorter side direction of the ultrasound emitting face 51 and in parallel to the longitudinal direction of the ultrasound emitting face 53. The same is true of the diagnostic transducer elements 52e through 52p. Each of the arrayed diagnostic transducer elements 52a through 52p converts electric signals, e.g. in a pulse form, from the transmitting/receiving device 12 into mechanical transducers, deflects them to transmit diagnostic ultrasounds to the subject, and at the same time receives reflected echo signals generated from the subject and converts them into electric signal pulses.

The backing material 54 is formed of, among other things, a low-impedance layer having a thickness of half the wavelength of the therapeutic ultrasounds, and disposed superposing over the reverse faces of the therapeutic transducer elements 50a through 50d to the ultrasound emitting faces 51. This causes ultrasounds to be transmitted to the side reverse to the emitting direction, out of the ultrasounds emitted from the therapeutic transducers 50, to be reflected by the backing material 54 and proceed towards the subject. Therefore, it is possible to efficiently emit therapeutic ultrasounds towards the subject.

Further, the cooling device 56 is disposed superposing over the reverse face of the backing material 54, i.e. the face reverse to the ultrasound emitting direction of the therapeutic transducers 50. The cooling device 56, formed of a Peltier element or the like, absorbs heat by the Peltier effect when a current is let flow through it, and radiates the heat into the external atmosphere. It can thereby restrain the temperature rise of the ultrasound probe 10.

Figure 3:
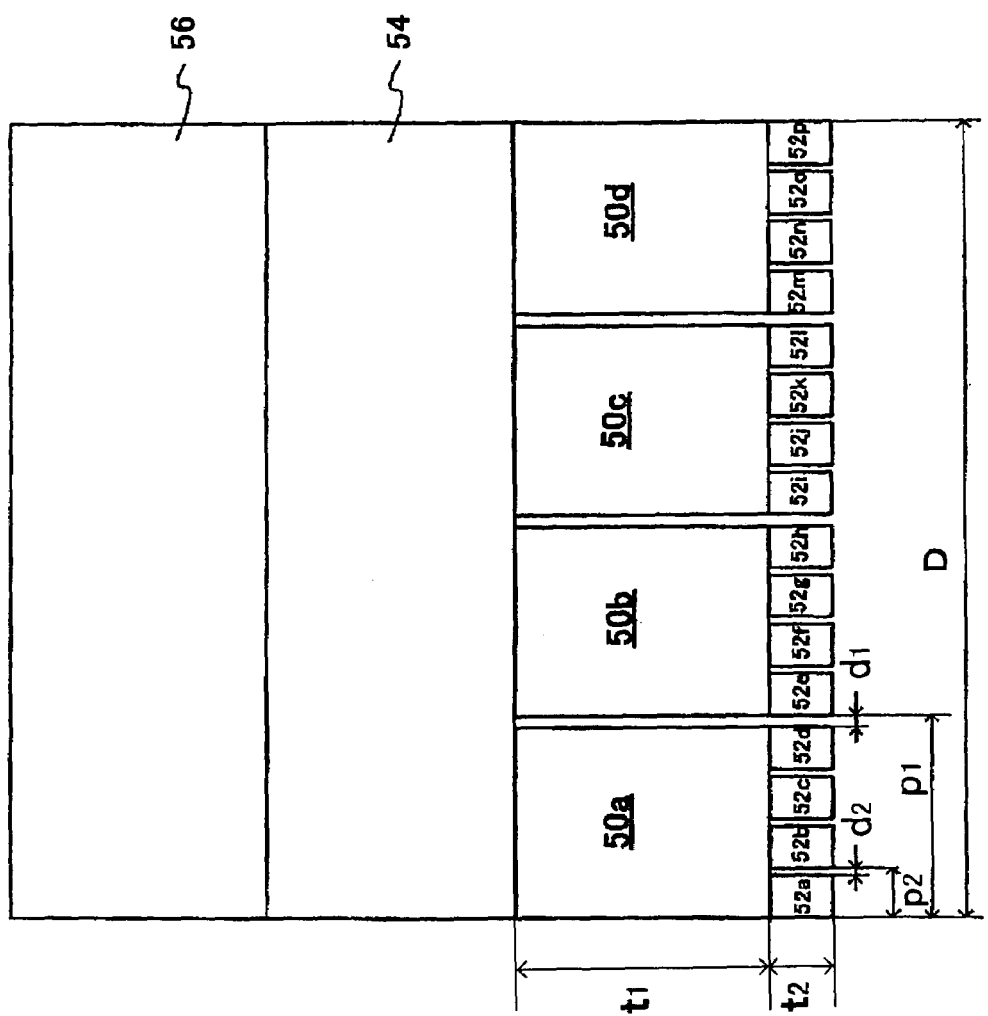
FIG. 3 is a sectional view along line III-III in FIG. 2.

One example of dimensions of such an ultrasound probe 10 will be described with reference to FIG. 3. The thickness $t_1$ of the therapeutic transducer elements 50a through 50d, the thickness $t_2$ of the diagnostic transducer elements 52a through 52p, the array pitch $p_1$ of the therapeutic transducer elements 50a through 50d and the array pitch $p_2$ of the diagnostic transducer elements 52a through 52p shown in FIG. 3 are set to be close to the respective values calculated by the following equations (1) through (4):

$$t_1 = \frac{\lambda_1}{2} = \frac{c}{2f_1} \quad (1)$$

$$t_2 = \frac{\lambda_2}{2} = \frac{c}{2f_2} \quad (2)$$

$$p_1 = \frac{cw}{2f_1} \quad (3)$$

$$p_2 = \frac{cw}{2f_2} \quad (4)$$

Here, $f_1$ is the frequency of the therapeutic ultrasounds emitted from the therapeutic transducers 50; $\lambda_1$, the wavelength of the therapeutic ultrasounds; $f_2$, the frequency of the diagnostic ultrasounds emitted from the diagnostic transducers 52; $\lambda_2$, the wavelength of the diagnostic ultrasounds; c, the longitudinal wave sound velocity of the therapeutic transducers 50 in the thickness direction, i.e. the ultrasound emitting direction; and cw, the sound velocity in water or in a living body.

In this embodiment, the frequency $f_1$ is supposed to be 500 kHz and the frequency $f_2$, 2 MHz. Therefore, if the sound velocity c is 3.3 mm/µs and the sound velocity cw, 1.538 mm/µs, the thickness $t_1$ will be 3.3 mm, the thickness $t_2$, 0.83 mm, the array pitch $p_1$, 1.54 mm and the array pitch $p_2$, 0.39 mm according to equations (1) through (4). Further, supposing that the number of the diagnostic transducers is 64, the array size, i.e. the ultrasound aperture D, of the ultrasound probe 10 shown in FIG. 3 will be D=64×$p_2$=24.6 mm. If the dimensions are such as stated above, even if, for example, the opening where the skull is thin and permits relatively ready transmission of ultrasounds (e.g. near the temples) is limited to 30 mm square for example, the ultrasound aperture D of the ultrasound probe 10 can be accommodated within that range. Therefore, the losses of the diagnostic ultrasounds and of the therapeutic ultrasounds due to the thickness of the skull can be reduced.

Although the number of the diagnostic transducers is supposed to be 64 and the ultrasound aperture D=64×$p_2$=24.6 mm in the case described above, the number N of the diagnostic transducers may be any desired natural number; it is possible to enlarge the ultrasound aperture D=N×$p_2$ by increasing the number N of the diagnostic transducers or, conversely, to narrow the ultrasound aperture D by reducing the number N of the diagnostic transducers.

Further, in order to improve the acoustic effect, the distances $d_1$ between the therapeutic transducer elements and the distances $d_2$ between the diagnostic transducer elements should be as narrow as practicable.

The frequencies of the ultrasounds to be used are determined from the viewpoints of effectiveness and safety. For example, where the limit value of the ultrasound intensity of the therapeutic ultrasounds is 720 mW/cm, in order to keep the temperature of the living tissue at 2° C. or less, the frequency $f_1$ is kept at 580 kHz or less. This makes it possible to keep the thermal index (TI), the indicator of the intensity of the thermal action of ultrasounds, at no more than 2. Further, the frequency $f_1$ is adjusted to 390 kHz or above. This makes it possible to keep the mechanical index (MI), the indicator of the intensity of the mechanical action of ultrasounds to destroy tissue cells by cavitations or the like arising within the blood vessel, at 0.25 or below.

With respect to the embodiment shown in FIGS. 2 and 3, an ultrasound probe 10 having four therapeutic transducer elements 50a through 50d and sixteen diagnostic transducer elements 52a through 52p was described, but the number of transducer elements of each type can be altered as appropriate. As shown in FIGS. 2 and 3, if the ratio between the array pitch of therapeutic transducer elements and the array pitch of diagnostic transducer elements is integral, the phase control system and the circuit form can be simplified.

Figure 4:
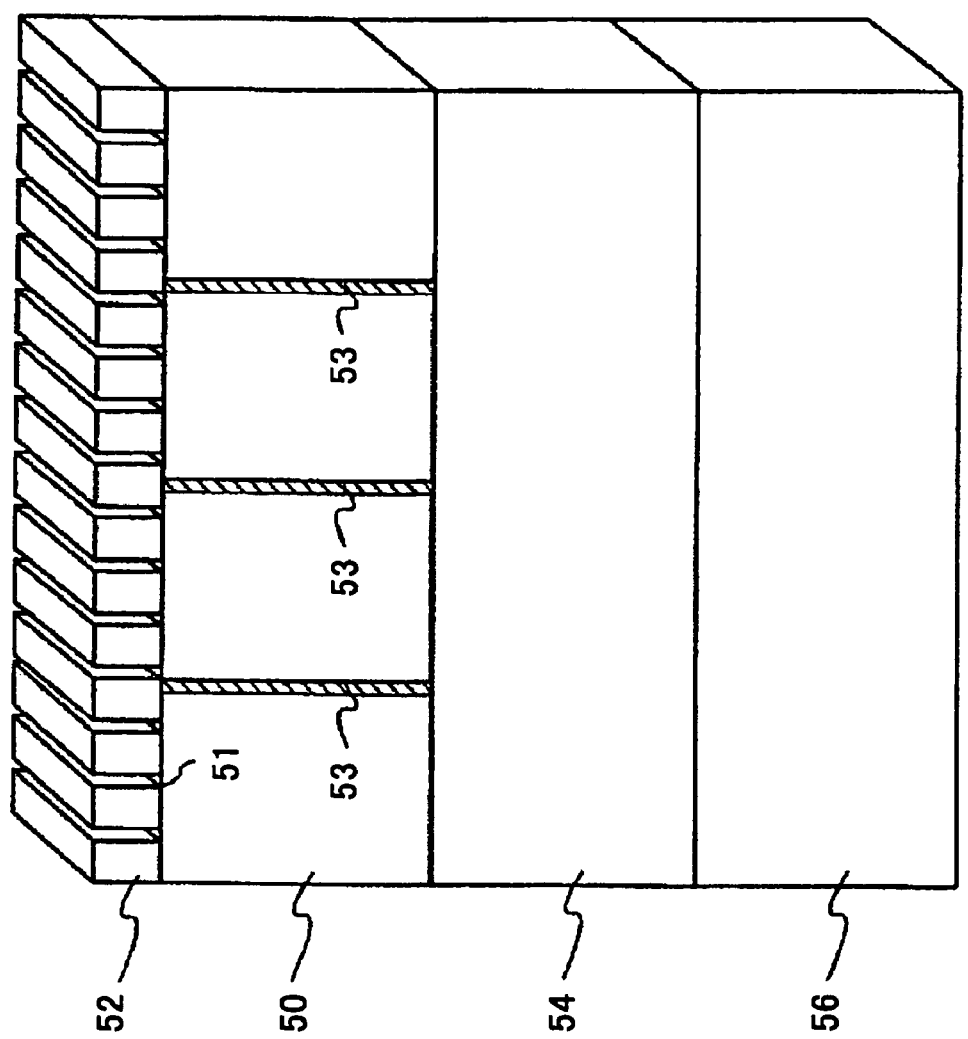
FIG. 4 is a perspective view schematically showing an ultrasound probe of another embodiment.

In the embodiment shown in FIG. 4, four therapeutic transducer elements and fifteen diagnostic transducer elements are disposed, sound insulators 53 are provided to fill the gaps between the therapeutic transducer elements and constitute the base of the diagnostic transducer elements. Examples of material for the sound insulators 53 include particulates of tungsten or the like and micro-balloons dispersed in epoxy resin. If the configuration is such that the ratio between the array pitch of therapeutic transducer elements and the array pitch of diagnostic transducer elements is not integral as shown in FIG. 4, an arrangement in which the gratings of the two types of transducer elements do not degenerate can be realized, and control can be so performed as not to let the grating lobes overlap each other.

Figure 5:
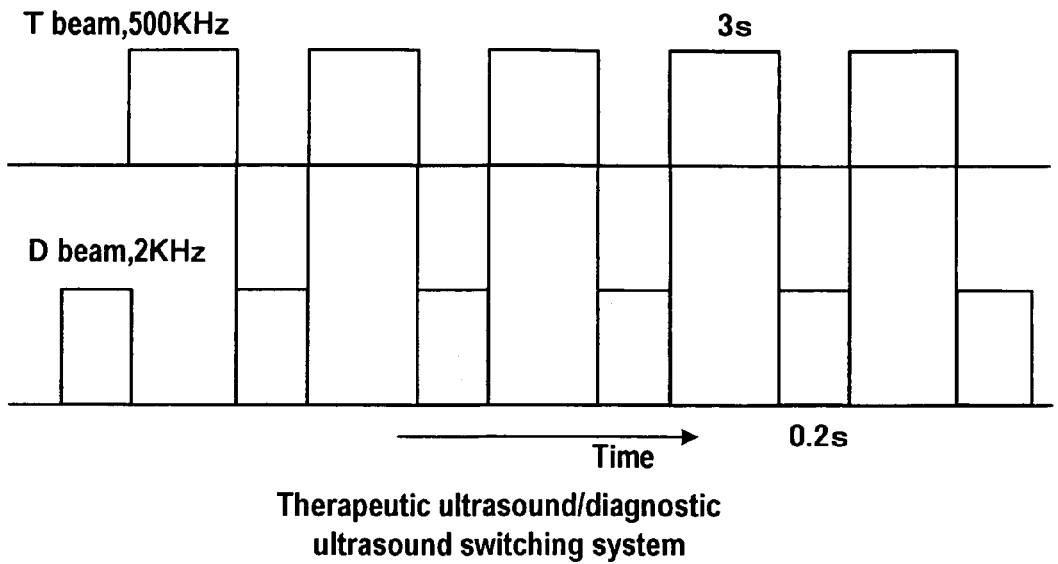
FIG. 5 is a time chart illustrating the operation of the ultrasound probe.

Next will be described the operations of the ultrasound probe 10 with reference to FIG. 5. Usually, when the therapeutic transducers 50 and the diagnostic transducers 52 are driven at the same time, therapeutic ultrasounds from the therapeutic transducers 50 are received by the diagnostic transducers 52 as noise. Therefore in this embodiment, as shown in FIG. 5, a therapeutic ultrasound beam (T beam) and a diagnostic ultrasounds beam (D beam) are alternately emitted, each at a set point of time. Incidentally, the emission timings of the T beam and the D beam may be altered as appropriate to prevent noise generation.

First, the D beam (e.g. 2 MHz in frequency) is emitted from the diagnostic transducers 52 for 0.2 second for example.

After the emission of the D beam, the T beam (e.g. 500 kHz in frequency) is emitted from therapeutic transducers 50 for 3 seconds for example. Repetition of such actions causes the D beam to form a tomogram and a two-dimensional blood stream image and the T beam to treat the target region. Incidentally, since it is sufficient for the duration of D beam emission to be long enough to form a tomogram or a two-dimensional blood stream image, the duration is set, for example, in a range of 0.01 to 0.2 second. The duration of T beam emission is set, for example, between 1 and 10 seconds as appropriate. To add, in order to improve the resolution of tomograms, the D beam is formed by transmitting at set intervals a burst wave consisting of pulse waveforms put together over ½ to 20 wavelengths, for example. The T beam is formed by transmitting consecutively transmitted ultrasounds so that a prescribed mechanical index can be secured.

In this embodiment, since the scanning coordinates of the T beam from the therapeutic transducers 50 and those of the D beam from the diagnostic transducers 52 can be so positioned as to coincide with each other, the position of irradiation with therapeutic ultrasounds can be more accurately controlled. Therefore, the target region whose position has been identified with the D beam can be accurately irradiated with the T beam.

Further, as it is possible to bring the center of the aperture of the therapeutic transducers 50 into coincidence with the center of the aperture of the diagnostic transducers 52, there is no particular need for coordinate conversion, and accordingly the control mechanism can be simplified.

Moreover, by electrically controlling the ultrasound probe 10 without having to move it along the body surface, tomograms are reconstructed by using the D beam and the target region can be treated by using the T beam. Therefore, the length of time required for treatment can be shortened, and the efficiency of ultrasound therapy can be enhanced in other ways as well. For example, whereas any cerebral thrombosis should be dissolved in a short period from the time when a cerebral infarction has occurred, the cerebral thrombosis can be dissolved promptly and accurately in this embodiment.

Figure 6:
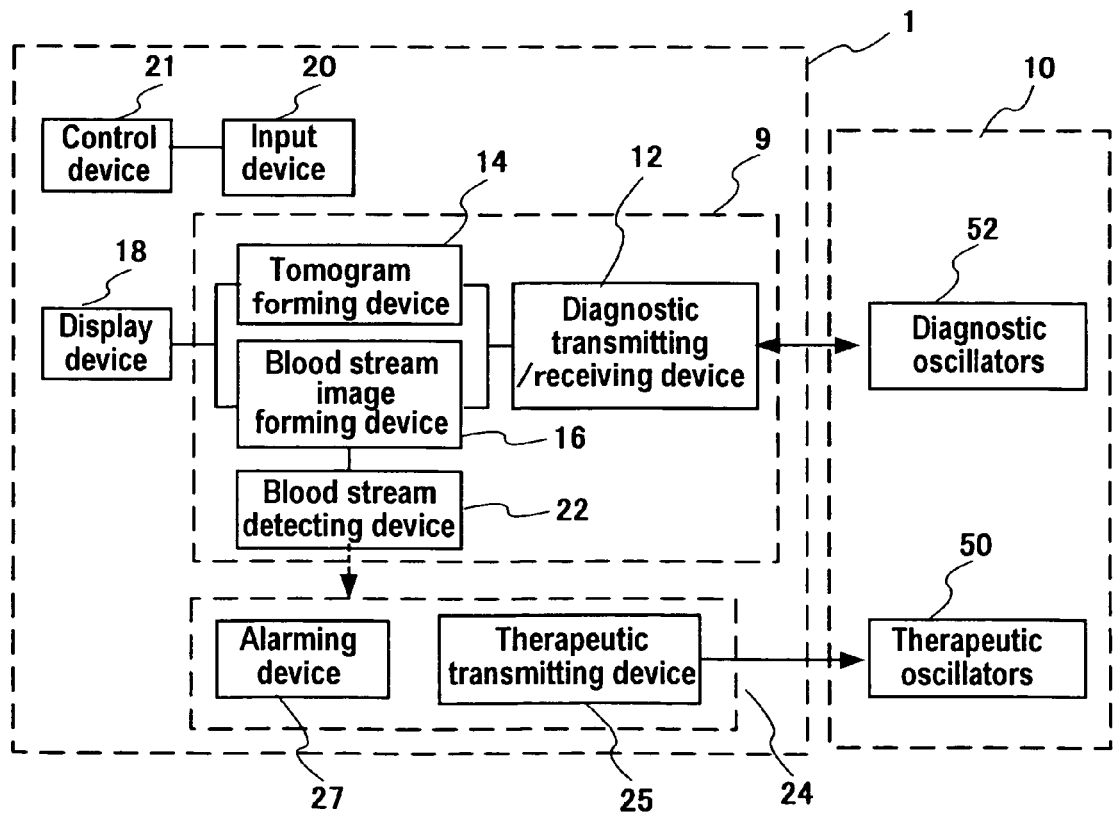
FIG. 6 is a configurative diagram of an ultrasound apparatus of a second embodiment according to the invention.

A second embodiment to which an ultrasound probe and an ultrasound apparatus according to the invention are applied will be described with reference to FIG. 6. This embodiment differs from the first embodiment in that, when a thrombosis has been dissolved and blood begins to flow, therapeutic ultrasounds are stopped or the amplitude of therapeutic ultrasounds is narrowed. FIG. 6 shows a configurative diagram of an ultrasound apparatus of this embodiment.

Usually, when any thrombosis has been dissolved with therapeutic ultrasounds, irradiation with therapeutic ultrasounds may be continued even after the thrombosis has been dissolved and blood begins to flow. In view of this possibility, a blood stream detecting device 22 is provided in this embodiment as shown in FIG. 6. The blood stream detecting device 22, which detects the intensity of the Doppler shift signal of reflected echo signals generated from the treated region, namely the blood stream velocity, outputs a control instruction to the therapeutic ultrasound transmitting unit 24 when the detected blood stream velocity is above a setpoint ($\alpha$).

If, for example, it is determined that the blood stream velocity detected by the blood stream detecting device 22 is not above the setpoint ($\alpha$), no control instruction is outputted to the therapeutic ultrasound transmitting unit 24. Therefore, the therapeutic transmitting device 25 maintains or increases the energy (e.g. amplitude or frequency) of therapeutic ultrasounds. Or if it is determined that the detected blood stream velocity is above the setpoint, a control instruction will be outputted to the therapeutic ultrasound transmitting unit 24, and the therapeutic transmitting device 25 will either reduce the energy or totally stop the emission of therapeutic ultrasounds. Then, the alarming device 27 issues a warning sound (e.g. buzz or voice) or displays a warning message on the display device 18.

In this embodiment, it is possible to detect dissolution of the thrombosis and the start of blood flowing. This enables the amplitude or frequency of therapeutic ultrasounds to be reduced or their emission to be stopped automatically when blood begins to flow. Therefore, the treated region can be prevented from excessively irradiated with therapeutic ultrasounds.

Incidentally, it is also conceivable to stop therapeutic ultrasounds manually when a warning sound or a warning message is issued. Although this embodiment has been described with the use of the ultrasound probe 10 of the first embodiment, the ultrasound apparatus of this embodiment can also be applied where the diagnostic probe and the therapeutic probe are separated from each other.

Figure 7:
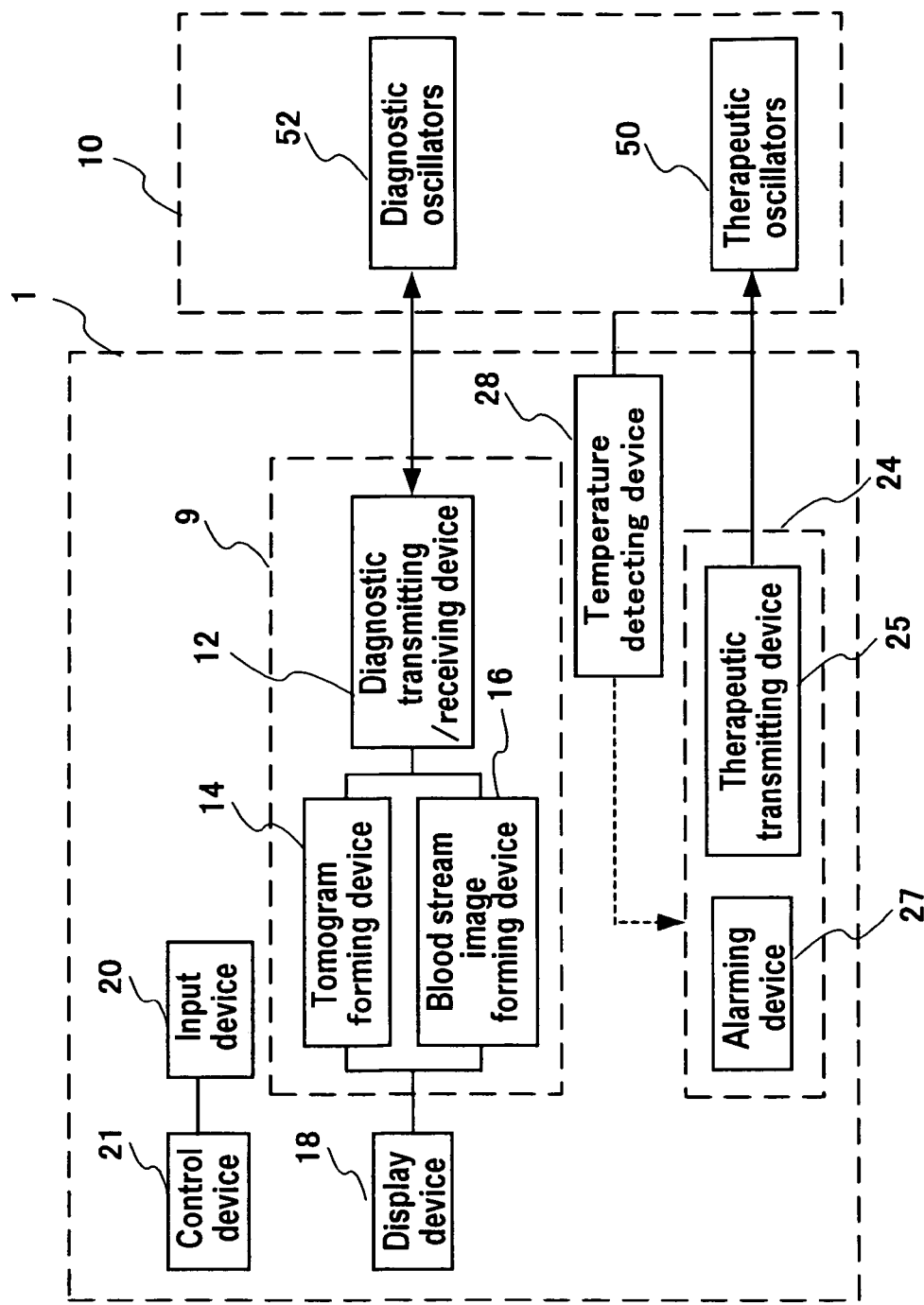
FIG. 7 is a configurative diagram of an ultrasound apparatus of a third embodiment according to the invention.

A third embodiment to which an ultrasound probe and an ultrasound apparatus according to the invention are applied will be described with reference to FIG. 7. This embodiment differs from the first embodiment in that, when the temperature of the ultrasound probe has risen above the set level, the frequency or amplitude of therapeutic ultrasounds is reduced or their emission is stopped. FIG. 7 shows a configurative diagram of an ultrasound apparatus in this embodiment.

Usually, when therapeutic and diagnostic ultrasounds are emitted from the ultrasound probe 10, part of the energy of the emitted ultrasounds is converted into thermal energy within the ultrasound probe 10. Therefore the temperature of the ultrasound probe 10 may rise. In view of this possibility, a temperature detecting device 28 is provided in this embodiment as shown in FIG. 7. The temperature detecting device 28, intended to detect the temperature of the ultrasound probe 10, outputs a control instruction to the therapeutic ultrasound transmitting unit 24 when the detected temperature exceeds a setpoint.

If, for example, it is determined that the temperature rise detected by the temperature detecting device 28 does not exceed a setpoint (e.g. 2° C.), no control instruction is outputted to the therapeutic ultrasound transmitting unit 24. Therefore, the therapeutic transmitting device 25 maintains or increases the energy (e.g. amplitude or frequency) of therapeutic ultrasounds. Or if it is determined that the detected temperature rise exceeds the setpoint, a control instruction will be outputted to the therapeutic ultrasound transmitting unit 24, and the therapeutic transmitting device 25 will either reduce the energy or totally stop the emission of therapeutic ultrasounds. Then, the alarming device 27 issues a warning sound (e.g. buzz or voice) or displays a warning message on the display device 18.

In this embodiment, since it is possible to automatically restrain the temperature rise of the ultrasound probe 10, the temperature rise can be prevented from inviting any side effect on the living tissue. Incidentally, instead of detecting the temperature of the ultrasound probe 10, the temperature of the water bag 32*a* shown in FIG. 1 can be detected. In short, the point is to detect a temperature correlated to the therapeutic transducers 50 or the diagnostic transducers 52.

Incidentally, it is also conceivable to stop therapeutic ultrasounds manually when a warning sound or a warning message is issued. Although this embodiment has been described with the use of the ultrasound probe 10 of the first embodiment, the ultrasound apparatus of this embodiment can also be applied where the diagnostic probe and the therapeutic probe are separated from each other.

Figure 8:
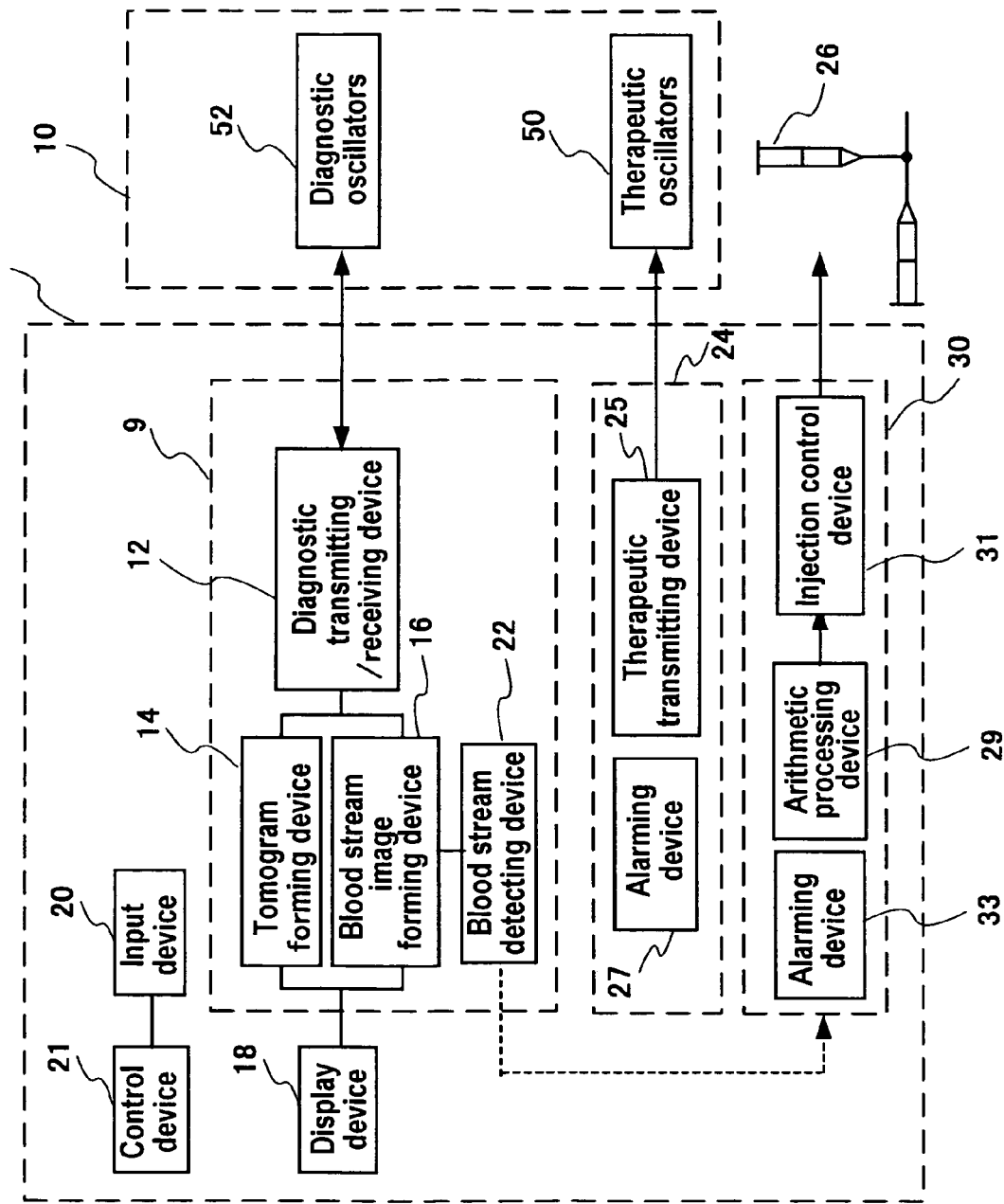
FIG. 8 is a configurative diagram of an ultrasound apparatus of a fourth embodiment according to the invention.

A fourth embodiment to which an ultrasound probe and an ultrasound apparatus according to the invention are applied will be described with reference to FIG. 8. This embodiment differs from the second embodiment in that, when the infarcted region is treated, a thrombolytic agent is used in combination, and the dose of thrombolytic agent is reduced or, its administration is stopped, when the thrombosis has dissolved. FIG. 8 shows a configurative diagram of an ultrasound apparatus in this embodiment.

Usually, when treating a thrombosis in an infarcted region, the thrombosis is irradiated with therapeutic ultrasounds, while a thrombolytic agent is injected into the subject to accelerate the dissolution of the thrombosis. In that case, the thrombolytic agent may continue to be injected into the subject even after the thrombosis has been dissolved and blood begins to flow.

In view of this possibility, a solvent injection control unit 30 is provided in this embodiment as shown in FIG. 8. The solvent injection control unit 30 has an injection control device 31, an arithmetic processing device 29, an alarming device 33 and so forth. The injection control device 31 controls the dose of the thrombolytic agent injected into the subject via an injector probe 26. The arithmetic processing device 29 computes the dose of the thrombolytic agent to be injected into the subject on the basis of a control instruction from the blood stream detecting device 22. The alarming device 33 sounds a warning buzzer or displays a warning message on the basis of a control instruction from the blood stream detecting device 22.

If, for example, it is determined that the blood stream velocity detected by the blood stream detecting device 22 does not exceed a setpoint ($\alpha$), no control instruction will be issued to the solvent injection control unit 30. Therefore, the injection control device 31 maintains or increases the dose of the thrombolytic agent. Or if it is determined that the detected blood stream velocity exceeds the setpoint ($\alpha$), a control instruction will be issued to the solvent injection control unit 30, and the injection control device 31 will decrease the injected dose or stop the injection of the thrombolytic agent on the basis of the dose computed by the arithmetic processing device 29. Further, the alarming device 33 issues a buzz or voice or displays a warning message on the monitor 18.

This embodiment enables the injected dose of the thrombolytic agent to be reduced or their emission to be stopped automatically when the thrombosis has been dissolved and blood begins to flow. Therefore, the living tissue can be prevented from suffering a side effect due to an excessive dose of the thrombolytic agent.

Incidentally, it is also conceivable to manually stop injecting the thrombolytic agent when a warning sound or a warning message is issued. Also, the injected dose of the thrombolytic agent may be displayed on the display screen of the monitor 18 on a real time basis. This would enable the operator to objectively keep track of the injected dose of the thrombolytic agent.

Although this embodiment has been described with the use of the ultrasound probe 10 of the first embodiment, the ultrasound apparatus of this embodiment can also be applied where the diagnostic probe and the therapeutic probe are separated from each other.

Figure 9:
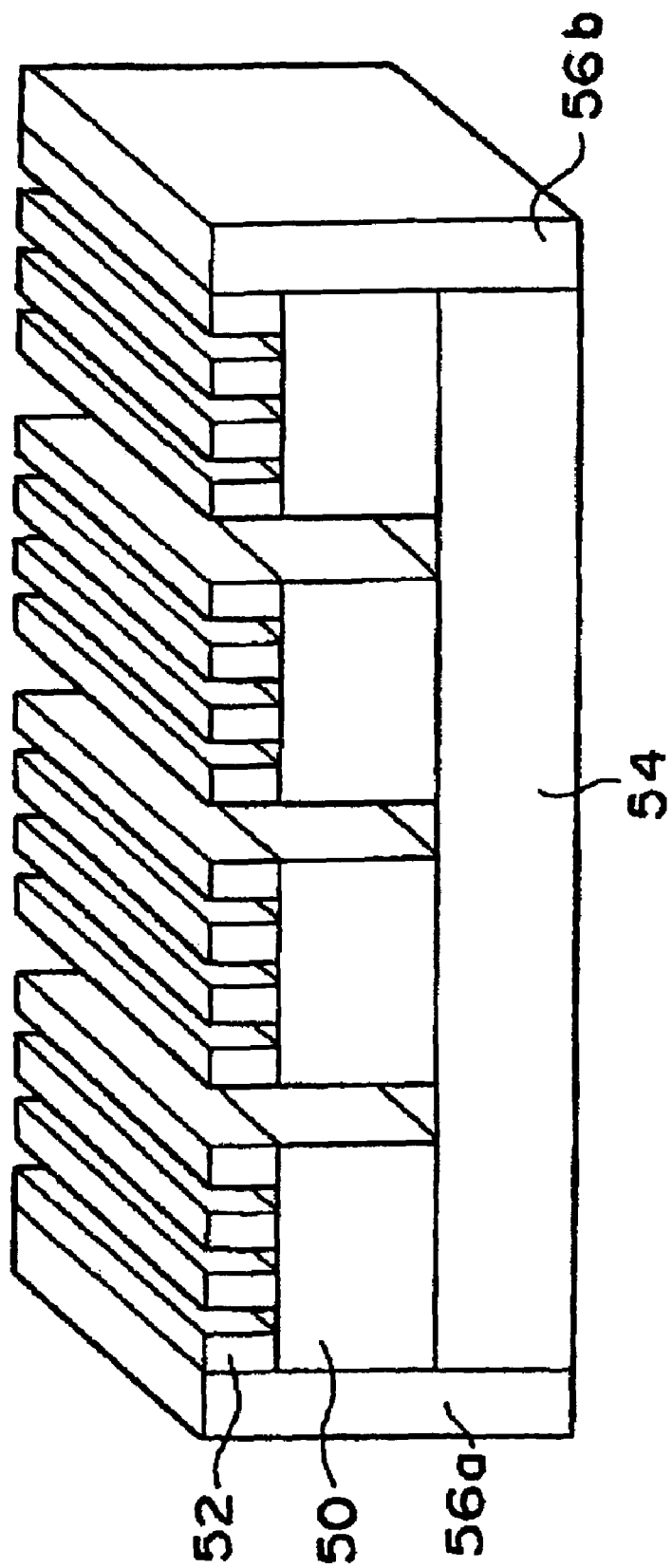
FIG. 9 is a perspective view schematically showing an ultrasound probe of a fifth embodiment according to the invention.
Figure 10:
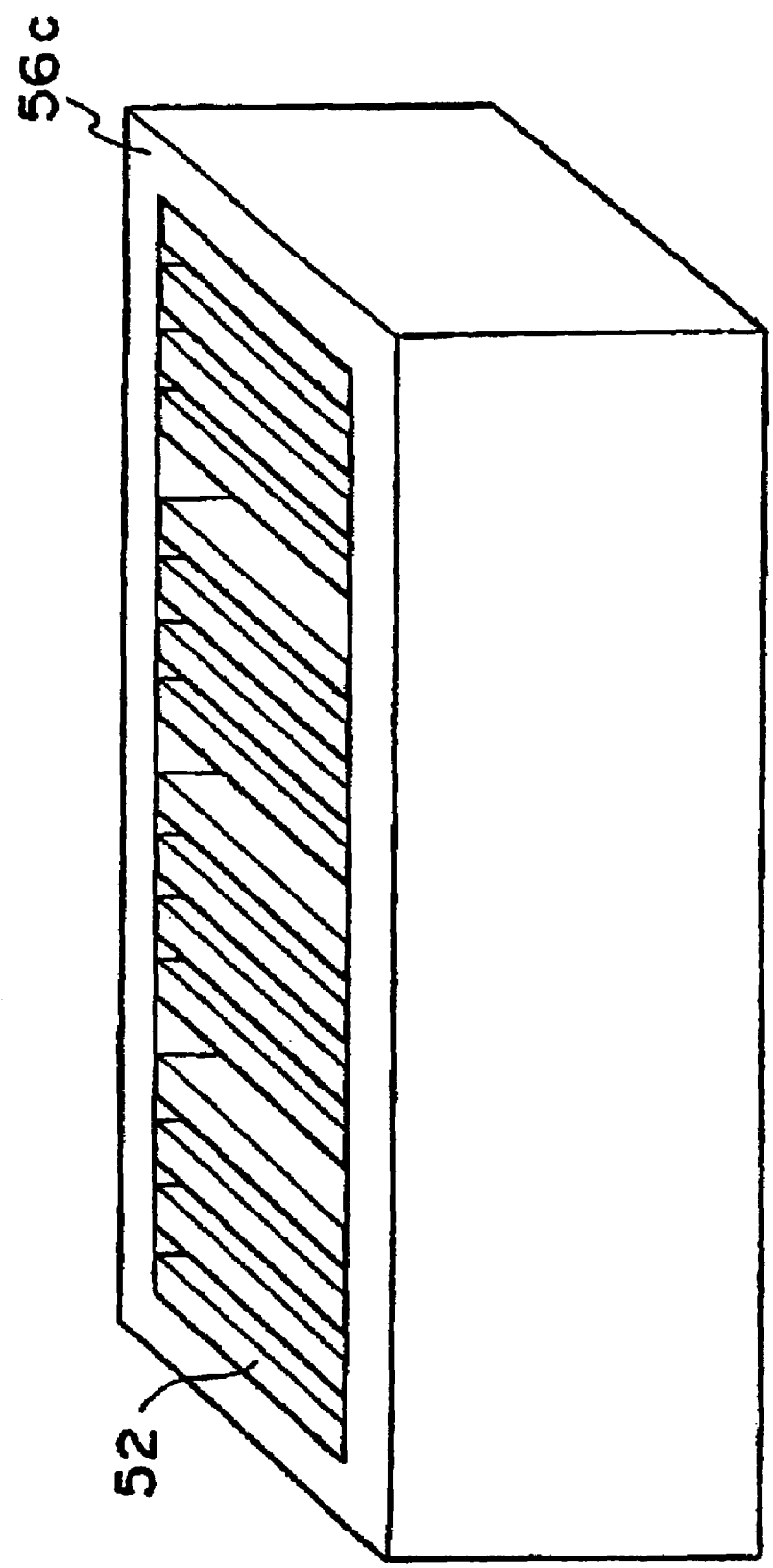
FIG. 10 is a perspective view schematically showing another example of an ultrasound probe of the fifth embodiment according to the invention.
Figure 11:
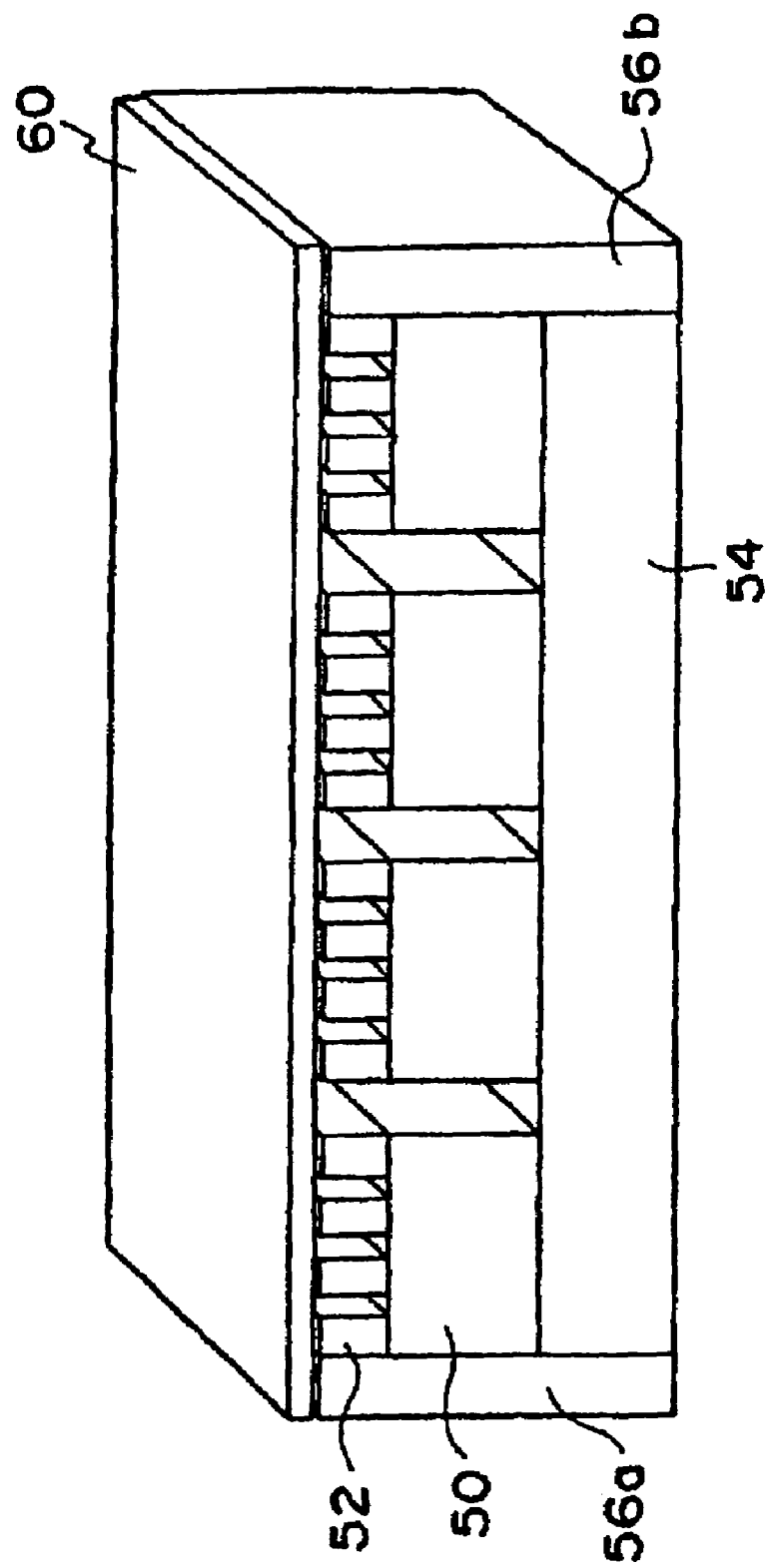
FIG. 11 is a perspective view schematically showing still another example of an ultrasound probe of the fifth embodiment according to the invention.

A fifth embodiment to which an ultrasound probe and an ultrasound apparatus according to the invention are applied will be described with reference to FIGS. 9 through 11. This embodiment differs from the first embodiment in that the installation of the cooling devices is positioned on sides of the therapeutic transducers and the diagnostic transducers. FIG. 9 shows the ultrasound probe in this embodiment.

As shown in FIG. 9, cooling devices 56a and 56b are disposed on two sides of the therapeutic transducers 50 and the diagnostic transducers 52. In this embodiment, the heat of the ultrasound probe 10 can be radiated into the external atmosphere by appropriately letting a current flow through the cooling devices 56a and 56b. Therefore, it is made possible to continuously irradiate the target region with ultrasounds for a relatively long time while keeping the temperature rise of the ultrasound probe 10 at or below a setpoint (e.g. 2° C.). As a result, the length of time required for therapy can be shortened, and the efficiency of treatment can be enhanced in other ways as well.

Further with respect to the cooling devices 56, they can be installed in any positions if only they can cool the therapeutic transducers 50 or the diagnostic transducers 52. For example, as shown in FIG. 10, a cooling device 56c can be so disposed as to cover sidewalls surrounding the ultrasound probe 10.

It is also possible to use a metallic foil in addition to the cooling devices. For example, as shown in FIG. 11, a metallic foil 60 is arranged over the ultrasound emitting faces of the diagnostic transducers 52 of FIG. 9. The metallic foil 60 so arranged is in contact with the cooling devices 56a and 56b. This enables the heat generated by the diagnostic transducers 52 to be absorbed by the metallic foil 60. The absorbed heat is guided to the cooling devices 56a and 56b via the metallic foil 60. The guided heat is radiated by the Peltier effect of the cooling devices 56a and 56b. Therefore, the temperature rise of the ultrasound probe 10 can be restrained. To add, the metallic foil 60 is a conductor (e.g. metal) thinned to a few $\mu$m, formed of a material which would not affect emission of ultrasounds.

Further, since the ultrasound emitting faces of the diagnostic transducers 52 are covered by the metallic foil 60, when the ultrasound probe 10 is brought into contact with the body surface, the temperature of the ultrasound probe 10 is not directly transmitted to the subject. Therefore, the temperature of the ultrasound probe 10 can be prevented from causing a side effect to the subject.

A sixth embodiment to which an ultrasound probe and an ultrasound apparatus according to the invention are applied will be described. This embodiment differs from the first through fifth embodiments in that therapeutic ultrasounds in a burst wave form are emitted to avoid occurrence of any side effect on the living tissue.

For example, where a cerebral infarction is to be treated, therapeutic ultrasounds brought incident into the brain from the ultrasound probe 10 may be reflected back by the inner wall of the skull in their proceeding direction. This would occur because the skull is higher in acoustic impedance than the living tissues within the brain. The superposing of reflected therapeutic ultrasounds (hereinafter referred to as reflected waves) over the therapeutic ultrasounds (hereinafter referred to as incident waves) brought incident into the brain from the ultrasound probe 10 and their mutual interference may give rise to standing waves within the brain. If the standing waves have a relatively high strength (amplitude) locally, they may bring on a side effect on the living tissues within the brain.

In view of this possibility, the therapeutic transmitting device 25 generates driving signals of a burst wave from the basic waveform in this embodiment. As the driving signals so generated are supplied to the therapeutic transducers 50, the burst wave is emitted from the therapeutic transducers 50 to the subject. The duration of the burst wave then is set to be relatively short (i.e. 10 $\mu$s), and the rest duration, relatively long (e.g. 100 $\mu$s to 300 $\mu$s). To add, a burst wave consisting of pulse waveforms put together in which, for example, the duration of one wavelength is 2 μs is emitted.

For example, where it takes the reflected waves 100 μs of time to return within the brain, the rest duration of the burst wave is set longer than 100 μs. Incidentally, the emitting duration and the rest duration of the burst wave, which are altered as appropriate, are set in advance from the input device 20.

In this embodiment, after an incident burst wave $T_n$ is reflected back, the next burst wave $T_{n+1}$ is brought to incidence. Therefore, the burst waves $T_n$ and $T_{n+1}$ do not overlap each other, so that any side effect on the living tissue can be avoided.

Therapeutic ultrasounds, in particular, are less susceptible to attenuation when proceeding within the brain, because their frequency is, for example, 500 kHz. Since the intensity of the reflected wave and that of the incident wave are approximately equal for this reason, the intensity of the interfering wave is relatively high. In this respect, this embodiment enables interference between the reflected wave and the incident wave of therapeutic ultrasounds to be averted.

Diagnostic ultrasounds, since their frequency is usually set to, for example, 2 MHz or above, are more susceptible to attenuation when proceeding within the brain. Therefore, the intensity of the interfering wave is relatively low and, as in the case of diagnostic ultrasounds, the rest duration of the pulse wave or the burst wave may be set relatively long.

Although the duration of burst wave emission is supposed to be 10 μs for example, it may be altered as appropriate. The point is that, the duration may be of any length only if, even when the incident wave and the reflected wave interfere with each other, it is made possible to keep the duration of the interfering wave short to avoid its side effect on the living tissue.

Although this embodiment has been described with the use of the ultrasound probe 10 of the first embodiment, the ultrasound apparatus of this embodiment can also be applied where the diagnostic probe and the therapeutic probe are separated from each other.

Figure 12:
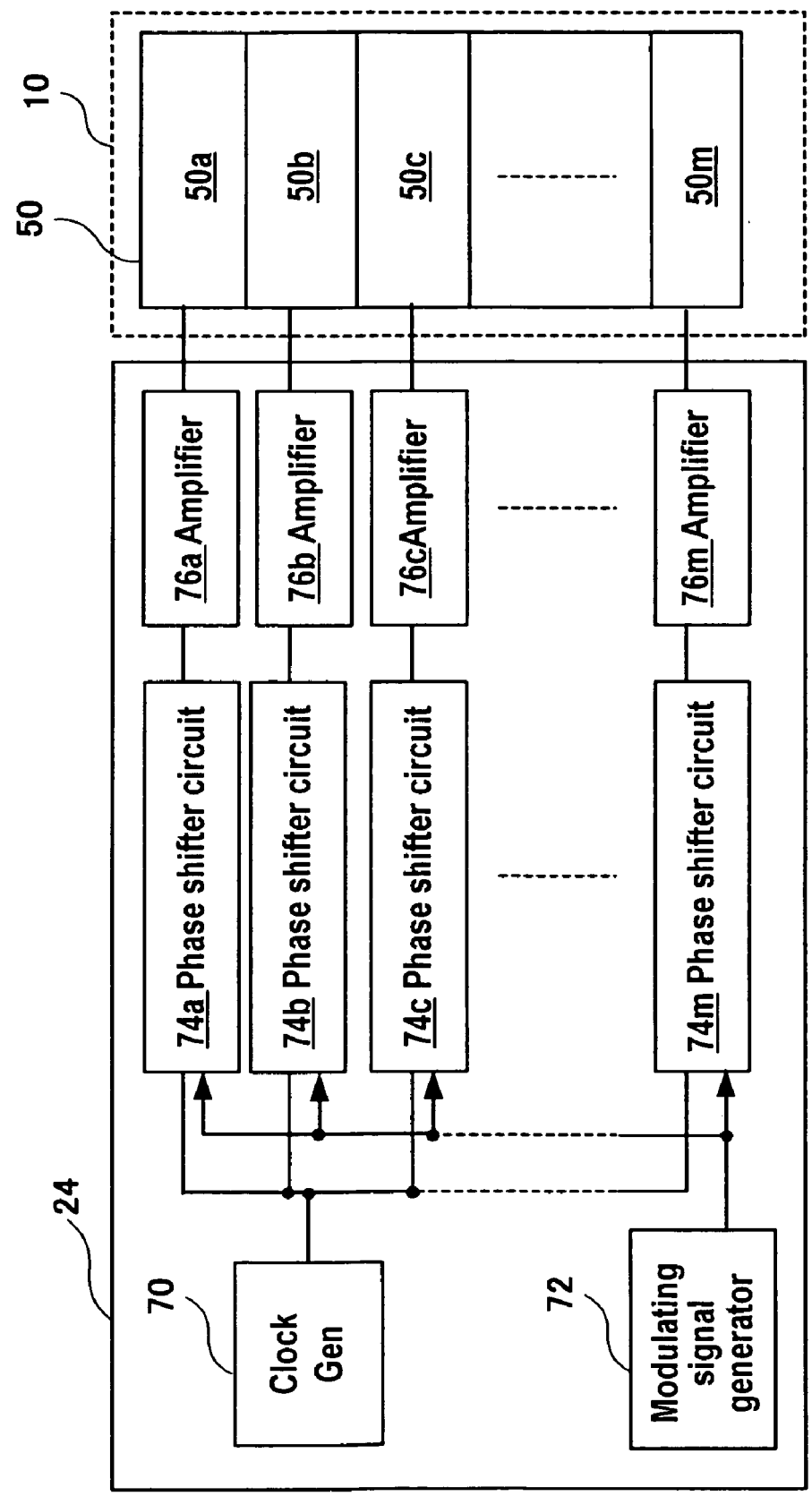
FIG. 12 is a configurative diagram of a therapeutic ultrasound transmitting unit of a seventh embodiment according to the invention.

A seventh embodiment to which an ultrasound probe and an ultrasound apparatus according to the invention are applied will be described with reference to FIG. 12. This embodiment differs from the sixth embodiment in that the frequency of therapeutic ultrasounds is gradually raised with the lapse of emission time. FIG. 12 shows a configurative diagram of the therapeutic transmitting device 25 of FIG. 1.

As shown in FIG. 12, the therapeutic ultrasound transmitting device 24 comprises a clock generator 70, a modulating signal generator 72, phase shifter circuits 74*a* through 74*m* (m: a natural number), amplifiers (hereinafter referred to as amplifiers 76*a* through 76*m*). Incidentally, the phase shifter circuits 74*a* through 74*m* can be formed of delay circuits. Sign m matches the number of therapeutic transducer elements 50*a* through 50*m* constituting the ultrasound probe 10.

First, the basic waveform of a continuous wave is generated by the clock generator 70. The generated basic waveform is shifted in phase by the phase shifter circuits 74*a* through 74*m*. And each shifted basic waveform, after being amplified by the amplifiers 76*a* through 76*m*, is inputted to the therapeutic transducers 50 as a driving signal. The inputted driving signals cause the therapeutic transducers 50 to emit therapeutic ultrasounds. With the lapse of the emission time, the modulating signal generator 72 generates modulating signals. The generated modulating signals are inputted to the phase shifter circuits 74*a* through 74*m*. With the inputted modulating signals, the phase shifter circuits 74*a* through 74*m* significantly modulate the frequencies of the basic waveforms. The modulated waveforms are inputted to the therapeutic transducers 50 as driving signals. This causes therapeutic ultrasounds whose frequencies are significantly modulated to be emitted from the therapeutic transducers 50. For example, the frequency of the ultrasounds at the starting time of emission (T=0) being represented by $f_0$ and their wavelength by $\lambda_0$, modulating signals are so generated by the modulating signal generator 72 that the frequency of the ultrasounds after the lapse of a certain period of time (T=10 μS) be $4f_0$ and their wavelength, $\lambda_0/4$. Repetition of such actions causes the therapeutic ultrasounds emitted from the therapeutic transducers 50 to be modulated in frequency in the direction of the time axis.

In this embodiment, even if, for example, the reflected wave and the incident wave overlap each other within the skull, the overlapping reflected wave and incident wave will differ in frequency. Since the interference pattern between the reflected wave and the incident wave therefore is not fixed, the intensity of the interference wave generated by the interference between the reflected wave and the incident wave can be restrained.

To add, whereas the timing of modulating the frequency can be set as appropriate, in this embodiment the frequency of therapeutic ultrasounds is modulated every time an emitted ultrasound is transmitted from the brain surface into the skull and proceeds into the brain (e.g. 10 μS) so that the inference pattern of the therapeutic ultrasounds may not be fixed at all. The point is that the frequency should be modulated in the direction of the time axis on the basis of the basic waveforms.

Incidentally, the modulation value of the frequency can be set as appropriate. For example, if the frequency is so modulated that the reflected wave and the incident wave deviated from each other by ¼ to ½ wavelength, the reflected wave and the incident wave will so interfere as to cancel each other. Therefore, the intensity of the interference wave can be further prevented from increasing.

Although this embodiment has been described with the use of the ultrasound probe 10 of the first embodiment, the ultrasound apparatus of this embodiment can also be applied where the diagnostic probe and the therapeutic probe are separated from each other.

Figure 13:
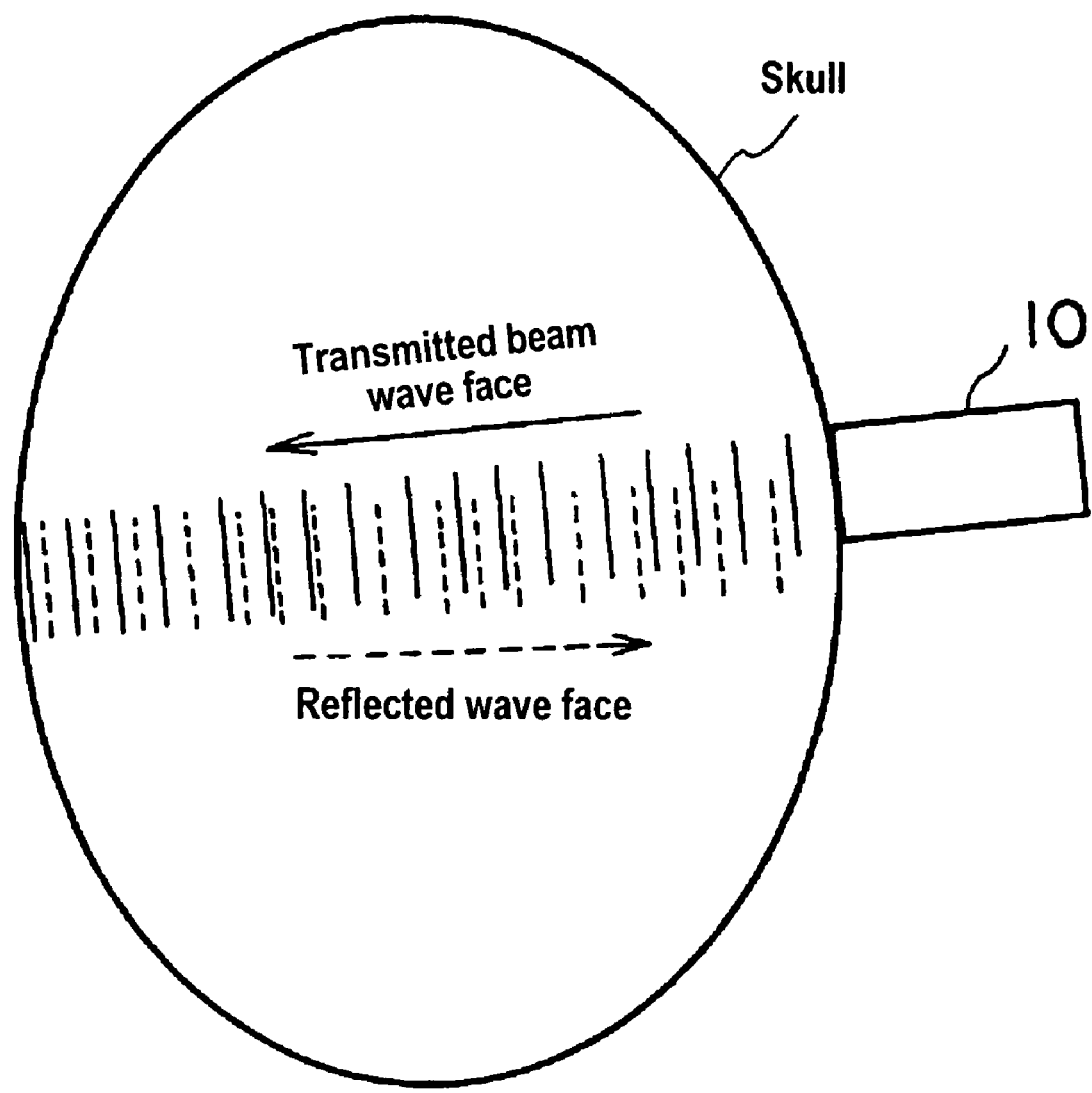
FIG. 13 is a diagram for describing the principle of avoiding interference between the incident wave and the reflected wave in an eighth embodiment according to the invention.

An eighth embodiment to which an ultrasound probe and an ultrasound apparatus according to the invention are applied will be described with reference to FIGS. 12 and 13. This embodiment differs from the seventh embodiment in that the incident direction of therapeutic ultrasounds is shifted at every set time. FIG. 13 is a diagram for describing the principle of avoiding interference between the incident wave and the reflected wave.

Thus, when driving signals are generated by the therapeutic ultrasound transmitting device 24 of FIG. 12, preset delay data are assigned to the phase shifter circuits 74*a* through 74*m* at every set time (e.g. 0.1 second). As this causes the ultrasounds emitted from the therapeutic transducers 50 to be deflected, the emitting direction of the ultrasound beam is altered. The angle (θ) of altering the ultrasound beam may be changed as appropriate.

In this embodiment, as shown in FIG. 13, the proceeding direction of the incident wave and that of the reflected wave of the therapeutic ultrasounds are no longer on the same straight line. Thus, since the incident wave and the reflected wave become different in direction, interference between the incident wave and the reflected wave can be avoided.

Further, although the set time for altering the emitting direction of ultrasounds is supposed to be 0.1 second in this embodiment, it can be set as appropriate. For example, if the incident wave and the reflected wave overlap and interfere with each other, the interference wave may generate cavitations (bubbles) in the blood vessel. The generated cavitations, after growing in size gradually, are ruptured. The impact of the cavitations may bring on a side effect on the living tissue. It is therefore desirable to alter the emitting direction of ultrasounds before cavitations arise.

Although this embodiment has been described with the use of the ultrasound probe 10 of the first embodiment, the ultrasound apparatus of this embodiment can also be applied where the diagnostic probe and the therapeutic probe are separated from each other.

Although the present invention has been hitherto described with reference to the first through eighth embodiments thereof, the invention is not limited to them. For example, besides cases of treating cerebral infarction, the ultrasound probe and the ultrasound apparatus according to the invention can also be applied to therapy of myocardial infarction. When treading myocardial infarction, the ultrasound probe is kept in contact with the chest, and diagnostic and therapeutic ultrasounds are emitted toward the thrombosis formed in the coronary artery through gaps between chest ribs.

The ultrasound probe and the ultrasound apparatus according to the invention can be applied not only to dissolving thromboses but also to dissolving abnormal solids formed within the body of inorganic substances or salts (e.g. calculi).

The ultrasound probe and the ultrasound apparatus according to the invention can also be used for cerebral infarctions of various types. Cerebral infarctions, for example, include lacunar infarction, atherothrombotic infarction and cardiogenic cerebral embolism. Lacunar infarction is a small infarcted focus formed in a deep part of the brain by the twining of a thin cerebral artery due to damage by high blood pressure. Atherothrombotic infarction occurs when the sclerosis of a carotid artery or a relatively thick artery within the skull (atherosclerosis) narrows that artery, inviting the formation of a thrombosis in that position to block the blood stream. Cardiogenic cerebral embolism is a blockade of the blood stream by a lump of blood (thrombosis) formed in the heart, peeled off and flowing into a cerebral artery. Whereas the thrombosis in the infarcted region should be dissolved in a short period from the time when a cerebral infarction has occurred in any of these types of cerebral infarction, the ultrasound probe and the ultrasound apparatus according to the invention can promptly and readily dissolve the thrombosis.

INDUSTRIAL APPLICABILITY

As hitherto described, the present invention makes it possible to realize an ultrasound probe and an ultrasound apparatus well suited to ultrasound therapy.

The invention claimed is:

1. An ultrasound probe, comprising:
a plurality of therapeutic transducers arrayed in a longitudinal direction of the ultrasound probe, for emitting therapeutic ultrasounds to a subject;
a plurality of diagnostic transducers arrayed in a longitudinal direction of the ultrasound probe, for emitting diagnostic ultrasounds to the subject and receiving the diagnostic ultrasounds reflected by the subject; and
sound insulators between the plurality of therapeutic transducers, wherein:
a stacking structure is provided where at least one of the diagnostic transducers is stacked over the top of one of the ultrasound emitting faces of the therapeutic transducers and over one of the sound insulators, and at least two of the diagnostic transducers are stacked over the ultrasound emitting face of the therapeutic transducers.

2. The ultrasound probe according to claim 1, wherein the ratio between the array pitch of the plurality of therapeutic transducers and the array pitch of the plurality of diagnostic transducers is not an integral ratio.

3. The ultrasound probe according to claim 1, further comprising a backing material having a thickness of half the wavelength of the therapeutic ultrasounds and disposed superposing over the reverse faces of the therapeutic transducers to the ultrasound emitting faces thereof.

4. The ultrasound probe according to claim 1, further comprising a cooling device or devices joined to at least either of the therapeutic transducers and the diagnostic transducers.

5. The ultrasound probe according to claim 4, wherein the cooling device or devices cover at least one of:
a reverse face to the ultrasound emitting face of at least either of the therapeutic transducers and the diagnostic transducers; and
a side face of at least either of the therapeutic transducers and the diagnostic transducers.

6. The ultrasound probe according to claim 4, further comprising a metallic foil in contact with the cooling device or devices over the ultrasound emitting face of at least either of the therapeutic transducers and the diagnostic transducers.

7. The ultrasound probe according to claim 1, wherein an ultrasound aperture D of the ultrasound probe is computed by:

$$D = N \times p_2$$

where N is the number of therapeutic transducers and $p_2$, the array pitch of the plurality of diagnostic transducers.

8. An ultrasound apparatus, comprising:
an ultrasound probe according to claim 1;
a therapeutic transmitting device for generating driving signals for the therapeutic transducers;
a diagnostic transmitting device for generating driving signals for the diagnostic transducers;
an image constructing device for reconstructing ultrasound images on the basis of reflected echo signals received by the diagnostic transducers; and
a detecting means for detecting the state of the therapy of the subject with the therapeutic ultrasounds, wherein
the therapeutic transmitting device has a warning function to output warning information on the basis of the state of the therapy detected by the detecting means.

9. The ultrasound apparatus according to claim 8, wherein the therapeutic transmitting device controls driving signals for the therapeutic transducers on the basis of the state detected by the detecting means.

10. The ultrasound apparatus according to claim 8, wherein the detecting means detects a temperature correlated to at least either of the therapeutic transducers and the diagnostic transducers and, when the detected temperature surpasses a setpoint, outputs the detected temperature to the therapeutic transmitting device.

11. The ultrasound apparatus according to claim 8, wherein the detecting means figures out the blood stream signal from the Doppler shift of reflected echo signals and, when the detected blood stream signal surpasses a setpoint, outputs the blood stream signal to the therapeutic transmitting device.

12. The ultrasound apparatus according to claim 11, further comprising an injection control device for controlling the dose of a thrombolytic agent to be injected into the subject, wherein the injection control device controls the injected dose of the thrombolytic agent on the basis of the blood stream signal detected by the detecting means.

13. The ultrasound apparatus according to claim 8, wherein the therapeutic transmitting device so generates driving signals for the therapeutic transducers as to prevent interference between a reflected wave reflected by a region in the subject and an incident wave brought to incidence into the subject from the therapeutic transducers.

14. The ultrasound apparatus according to claim 13, wherein the therapeutic transmitting device generates the driving signals of either a pulse wave or a burst wave from a basic waveform by controlling the duration of emission and the duration of rest.

15. The ultrasound apparatus according to claim 13, wherein the therapeutic transmitting device generates the driving signals for ultrasounds resulting from modulation of frequencies in the direction of the time axis on the basis of the basic waveform.

16. The ultrasound apparatus according to claim 13, wherein the therapeutic transmitting device so generates the driving signals as to differentiate the emitting direction of ultrasound beams emitted from the therapeutic transducers from the direction of the reflected wave reflected by a region in the subject.

\* \* \* \* \*